(12) United States Patent
Wada

(10) Patent No.: US 9,151,706 B2
(45) Date of Patent: Oct. 6, 2015

(54) METHOD OF DETERMINING FATIGUE CRACK LIFETIME IN HIGH-PRESSURE HYDROGEN ENVIRONMENT

(75) Inventor: Yoru Wada, Muroran (JP)

(73) Assignee: THE JAPAN STEEL WORKS, LTD., Tokyo (JP)

( * ) Notice: Subject to any disclaimer, the term of this patent is extended or adjusted under 35 U.S.C. 154(b) by 0 days.

(21) Appl. No.: 14/002,776

(22) PCT Filed: Mar. 1, 2012

(86) PCT No.: PCT/JP2012/055243
§ 371 (c)(1),
(2), (4) Date: Sep. 3, 2013

(87) PCT Pub. No.: WO2012/121106
PCT Pub. Date: Sep. 13, 2012

(65) Prior Publication Data
US 2013/0333481 A1 Dec. 19, 2013

(30) Foreign Application Priority Data
Mar. 4, 2011 (JP) .................................. 2011-047417

(51) Int. Cl.
*G01N 17/00* (2006.01)
*G01N 33/20* (2006.01)
*G01N 3/32* (2006.01)

(52) U.S. Cl.
CPC ................. *G01N 17/00* (2013.01); *G01N 3/32* (2013.01); *G01N 33/20* (2013.01); *G01N 2203/0066* (2013.01); *G01N 2203/0073* (2013.01); *G01N 2203/0232* (2013.01)

(58) Field of Classification Search
CPC  G01N 19/08; G01N 2203/0066; G01N 23/02

USPC ........................................................... 73/799
See application file for complete search history.

(56) References Cited

U.S. PATENT DOCUMENTS 4,121,953 A * 10/1978 Hull .............................. 148/329
5,505,095 A    4/1996 Raymond
(Continued)

FOREIGN PATENT DOCUMENTS

| DE | 10 2005 020 128 A1 | 11/2006 |
| JP | 2005024371 A | 1/2005 |
| JP | 2009025213 A | 2/2009 |

OTHER PUBLICATIONS

Search Report dated Jul. 18, 2014 issued by the European Patent Office in corresponding European Application No. 12754698.4.
(Continued)

*Primary Examiner* — Lisa Caputo
*Assistant Examiner* — Octavia Hollington
(74) *Attorney, Agent, or Firm* — Sughrue Mion, PLLC

(57) ABSTRACT

In a method of determining a fatigue crack lifetime of a low-alloy steel material coming in contact with high-pressure hydrogen in a high-pressure hydrogen environment, estimate a fatigue crack acceleration starting point $K_{max}^T$ of the low-alloy steel material using a crack-growth threshold stress intensity factor $K_{IH-R}$ obtained through a rising load test on the low-alloy steel material in a high-pressure hydrogen environment. The high-pressure hydrogen environment of the rising load test is a high-pressure hydrogen environment which has the same pressure and atmosphere as in the high-pressure hydrogen environment in which $K_{max}^T$ is estimated and in which the test temperature tolerance between both environments is ±5° C.

13 Claims, 12 Drawing Sheets

(56) References Cited

U.S. PATENT DOCUMENTS

| | | | |
|---|---|---|---|
| 5,585,570 A * | 12/1996 | Raymond | 73/851 |
| 7,035,746 B2 * | 4/2006 | Wada et al. | 702/82 |
| 7,889,840 B2 * | 2/2011 | Vasudevan et al. | 378/58 |
| 8,190,378 B2 * | 5/2012 | Sakai et al. | 702/35 |
| 8,234,930 B2 * | 8/2012 | Wada et al. | 73/807 |
| 8,313,589 B2 * | 11/2012 | Takasawa et al. | 148/330 |
| 2005/0028882 A1 | 2/2005 | Wada et al. | |
| 2011/0167921 A1 | 7/2011 | Wada et al. | |

OTHER PUBLICATIONS

Yasuo Manabe et al., "Development of 100MPa Class High Hydrogen Pressure Testing Equipment", R&D Kobe Steel Technical Report, vol. 58, No. 2, Aug. 2008, 5 pgs. total, XP055128456.

Yoru Wada, et al., "Fracture toughness characterization of hydrogen embrittled Cr-Mo steel", Strength, Fracture and Complexity, vol. 1, No. 3, Jan. 1, 2003, 7 pgs. total, XP055128265.

Wei, R. P., "On Understanding Environment-Enhanced Fatigue Crack Growth—A Fundamental Approach," Fatigue Mechanisms, Proceedings of an ASTM-NBS-NSF Symposium, Kansas City, Mo., May 1978, J. T. Fong, Ed., ASTM STP675, American Society for Testing and Materials, 1979, pp. 816-840.

2007 ASME Boiler and Pressure Vessel Code, 2009b Addenda, Rules for Construction of Pressure Vessels, "Article KD-10 Special Requirements for Vessels in High pressure Gaseous Hydrogen Transport and Storage Service," The American Society of Mechanical Engineers, Jul. 1, 2009, 6 pages total.

Takao Aoki et al., "Atsuryoku Yokiko no Suiso Zeika Kanjusei Hyoka ni Okeru Shomondai", Nippon Zairyo Kyodo Gakkai Gakujutsu Koenkai Ronbunshu, Jun. 16, 1988, pp. 49-52.

Yoshikuni Murakami et al., "Rising load test method to evaluate hydrogen embrittlement susceptibility of Cr-Mo steel", Journal of the Iron and Steel Institute of Japan, Mar. 5, 1984, vol. 70, No. 5, p. S639 (2 pages total).

Written Opinion issued Apr. 17, 2012, by the International Searching Authority in corresponding application No. PCT/JP2012/055243.

Search Report issued Apr. 17, 2012, by the International Searching Authority in corresponding application No. PCT/JP2012/055243.

The High Pressure Gas Safety Institute of Japan, "Standard of Ultrahigh-Pressure Gas Installations", Sep. 16, 2004, 9 pages total.

Takeshi Kunio et al. (ed.), "Fracture Mechanics Laboratory Procedure", Asakura Shoten, Jun. 20, 1984, 12 pagges total.

Yasuo Manabe et al., "Development of 100MPa Class High Hydrogen Pressure Testing Equipment (Special issue: Industrial Machines)", R&D Kobe Steel Technical Report, R&D Kobe Steel Technical Report 58(2), 19-23, Aug. 2008, Kobe Steel, Ltd.,, 5 pages total.

Seiji Fukuyama et al., "Fatigue Crack Growth of SNCM 439 Steel in High Pressure Hydrogen at Room Temperature", materials 34(381), pp. 709-714 (1985), 6 pages total.

The Japan Pressure Vessel Research Council (JPVRC), Division of Materials Science and Technology, Hydrogen Gas Embrittlement Technical Committee, Task Group V, "Measurement and evaluation of lower-limit stress intensity factor KIH based on hydrogen gas embrittlement cracking of 2-1/4Cr-1Mo steel", pp. 16-35 (1989), 39 pages total.

The High Pressure Gas Safety Institute of Japan, "Reports of Technological Examination Committee on Hydrogen Gas Stand Standard" and "Technological Examination Committee on Hydrogen Container for Fuel Cell", Dec. 2002, 6 pages total.

\* cited by examiner (a)

(b)

(c)

(d)

(e)

METHOD OF DETERMINING FATIGUE CRACK LIFETIME IN HIGH-PRESSURE HYDROGEN ENVIRONMENT

TECHNICAL FIELD

The present invention relates to a method of determining a fatigue crack lifetime which can be applied to a fatigue crack lifetime design or a fatigue crack lifetime diagnosis of a material used in a high-pressure hydrogen environment, and more particularly, to a method of determining a fatigue crack lifetime of a pressure vessel or a pressure component formed of low-alloy steel.

BACKGROUND ART

Recently, hydrogen has attracted attention as alternative energy to oil. For high-pressure hydrogen equipment such as pressure accumulators or pipes for storing and supplying hydrogen at a high pressure, there is a demand for materials exhibiting high resistance to high-pressure hydrogen at low cost. However, most metal materials exhibiting brittleness (=hydrogen environment brittleness) to high-pressure hydrogen gas and even materials exhibiting slight hydrogen environment brittleness to hydrogen have to be actually used for economical reasons. Such materials should be verified to be safe in practical use.

A drawing qualitatively showing fatigue crack growth characteristics in high-pressure hydrogen gas is shown in NPL 1 or the like.

A method and a procedure of selecting a material to be used and limiting a usage count, a lifetime, and the like thereof on the basis of test data in a hydrogen gas environment for materials likely to be embrittled in the high-pressure hydrogen gas are disclosed in NPL 2, and the procedure is shown in FIG. 12. In this method, a delayed crack test method of driving a bolt or a wedge into a block with a crack formed therein to load the block, maintaining the resultant block for 1000 hours or more, and acquiring a crack-growth threshold stress intensity factor $K_{IH-H}$ is performed (step s101). A fracture-limit crack depth $a_c$ of equipment is acquired from the crack-growth threshold stress intensity factor $K_{IH-H}$ (step s102) and an initially-estimated crack depth $a_0$ is calculated from the inspection limit (step s103).

Subsequently, a fatigue crack growth test in high-pressure hydrogen is performed in conditions of arbitrary repetition cycle times or literature data is acquired (step s104). Conditions of pressure P and stress ratio R (minimum load/maximum load) of actual equipment are set (step s105). Subsequently, a fatigue crack growth analysis is performed on area I, that is, a section of $(1-R) \times K_0(a_0)$ to $(1-R) \times K_{IH-H}(a_c)$, in the da/dN-ΔK diagram obtained in step s104 (step s106). From this analysis result, the fatigue crack lifetime (repetitive filling lifetime) until the initially-estimated crack depth $a_0$ reaches the fracture-limit crack depth $a_c$ or the depth corresponding to 80% of the plate thickness is calculated (step s107). It is determined that the equipment can be safely used when the lifetime is larger than the usage count (YES in step s107), and it is determined that a crack inspection should be carried out or use thereof should be stopped when the usage count reaches the lifetime (NO in step s107). The same test method as described above is disclosed in NPL 3.

CITATION LIST

Non Patent Literature

NPL 1: Wei, R. P., "On Understanding Environment-Enhanced Fatigue Crack Growth-A Fundamental Approach, "Fatigue Mechanisms, Proceedings of an ASTM-NBS-NSF symposium, Kansus City, Mo., May 1978, J. T. Fong, Ed., ASTM STP675, American Society for Testing and Materials, 1979, pp. 816-840

NPL 2: ASME, "ASME Boiler & Pressure Vessel Code, 2007 edition, Sec. VIII Div. 3, ARTICLE KD10", (2007) ASME NPL 3: The High Pressure Gas Safety Institute of Japan, "Reports of Technological examination committee on hydrogen gas stand standard and Technological examination committee on hydrogen container for fuel cell", p17-p18 (2002)

NPL 4: The Japan Pressure Vessel Research Council (JPVRC), Division of Materials Science and Technology, Hydrogen gas embrittlement Technical Committee, Task Group V, "Measurement and evaluation of crack lower-limit stress intensity factor KIH based on hydrogen gas embrittlement of 2.1/4Cr-1Mo steel", pp. 16-35 (1989)

NPL 5: Seiji FUKUYAMA, Kiyoshi YOKOGAWA, Michio ARAKI, "Fatigue crack growth in room-temperature high-pressure hydrogen environment of SNCM439 steel", materials 34(381), pp. 709-714 (1985)

NPL 6: Yasuo MANABE, Yasuhide MIYASHITA, "Development of 100 MPa high-pressure hydrogen tester (Special issue: Industrial Machines)", R&D Kobe Steel Technical Report, R&D Kobe Steel Technical Report 58(2), 19-23, 2008-08, Kobe Steel, Ltd.

NPL 7: Takeshi KUNIO, Hajime NAKAZAWA, Ikuhiko HAYASHI, Hiroyuki OKAMURA, "Fracture mechanics laboratory procedure", Asakura Shoten (1984), p. 250

NPL 8: The High Pressure Gas Safety Institute of Japan, "Standard of ultrahigh-pressure gas installations", KHK(S) 0220(2004), September, Heisei 16, The High Pressure Gas Safety Institute of Japan, p. 173-174

SUMMARY OF INVENTION

Technical Problem

However, the delayed crack test result at a high hydrogen pressure of 90 MPa shown in FIG. 1 of NPL 1 greatly deviates depending what materials are used in the delayed crack test. Since the fatigue crack growth rate at a high hydrogen pressure of 90 MPa shown in the drawing varies depending on the materials or the test conditions, the fatigue crack growth behavior is not sufficiently explained and it is thus difficult to actually evaluate the fatigue crack lifetime.

Therefore, it is necessary to provide a procedure and a method capable of qualitatively evaluating the fatigue crack lifetime with high accuracy.

The evaluation method, shown in the procedure of FIG. 12, using a related-art delayed crack test and an in-hydrogen fatigue crack growth test requires a large amount of test time and cost. Accordingly, when it is intended to accelerate research and development of materials for hydrogen energy, there is a need for establishment of an acceleration test method and an evaluation procedure capable of evaluating a fatigue crack lifetime at low cost for a short time.

The invention is made in view of the above-mentioned circumstances, and one object thereof is to provide a method of determining a fatigue crack lifetime which can accurately determine a fatigue crack growth lifetime of a low-alloy steel pressure component, which is provided for high-pressure hydrogen, in high-pressure hydrogen without depending on the steel type, the strength of the material, and the test conditions.

Another object of the invention is to provide a method of determining a fatigue crack lifetime which can predict a fatigue crack growth behavior in high-pressure hydrogen in a long cycle time corresponding to operation conditions of actual equipment from a short-time acceleration test.

Solution to Problem

That is, according to a first aspect of the invention, there is provided a method of determining a fatigue crack lifetime of a low-alloy steel material that comes in contact with high-pressure hydrogen in a high-pressure hydrogen environment, comprising: estimating a fatigue crack acceleration starting point $K_{max}^T$ of the low-alloy steel material using a crack-growth threshold stress intensity factor $K_{IH-R}$ obtained through a rising load test on the low-alloy steel material in a high-pressure hydrogen environment, wherein the high-pressure hydrogen environment of the rising load test is a high-pressure hydrogen environment which has the same pressure and atmosphere as in the high-pressure hydrogen environment in which $K_{max}^T$ is estimated and in which the test temperature tolerance between both environments is ±5° C.

According to a second aspect of the invention, in the method of determining a fatigue crack lifetime in a high-pressure hydrogen environment according to the first aspect, wherein the high-pressure hydrogen environment of the rising load test is an environment of ultrapure hydrogen of 99.9999 vol % or more.

According to a third aspect of the invention, in the method of determining a fatigue crack lifetime in a high-pressure hydrogen environment according to the first aspect, wherein the high-pressure hydrogen environment of the rising load test has an oxygen concentration of 1 ppm or less.

According to a fourth aspect of the invention, in the method of determining a fatigue crack lifetime in a high-pressure hydrogen environment according to the first aspect, wherein the test temperature of the rising load test is 23° C.±5° C.

According to a fifth aspect of the invention, in the method of determining a fatigue crack lifetime in a high-pressure hydrogen environment according to the first aspect, wherein the rising load test is performed at a strain rate of dK/dt=0.08 MPa-m$^{1/2}$/s or less for a short time (1 hour or less).

According to a sixth aspect of the invention, in the method of determining a fatigue crack lifetime in a high-pressure hydrogen environment according to the first aspect, wherein the estimating of the fatigue crack acceleration starting point is performed with a correlation that the fatigue crack acceleration starting point $K_{max}^T$ substantially agrees to the crack-growth threshold stress intensity factor $K_{IH-R}$.

According to a seventh aspect of the invention, in the method of determining a fatigue crack lifetime in a high-pressure hydrogen environment according to the first aspect, wherein a fatigue crack lifetime analysis is performed in a section of $(1-R) \times K_0(a_0)$ to $(1-R) \times K_{max}^T(a_c)$ in a fatigue crack growth characteristic diagram representing a relationship between a crack growth rate da/dN and a stress intensity factor width ΔK obtained through a fatigue crack growth test in a high-pressure hydrogen environment, wherein R represents a stress ratio, $K_0(a_0)$ represents a fatigue crack-growth threshold stress intensity factor based on an initially-estimated crack depth $a_0$, and $K_{max}^T(a_c)$ represents a fatigue crack acceleration starting point based on a fracture-limit crack depth $a_c$.

According to an eighth aspect of the invention, in the method of determining a fatigue crack lifetime in a high-pressure hydrogen environment according to the seventh aspect, wherein the initially-estimated crack depth is obtained from an inspection limit value based on a predetermined crack inspection.

According to a ninth aspect of the invention, in the method of determining a fatigue crack lifetime in a high-pressure hydrogen environment according to the seventh aspect, wherein the fracture-limit crack depth $a_c$ is calculated from the crack-growth threshold stress intensity factor $K_{IH-R}$.

According to a tenth aspect of the invention, in the method of determining a fatigue crack lifetime in a high-pressure hydrogen environment according to the seventh aspect, wherein the repetition count in which the initially-estimated crack depth $a_0$ reaches the fracture-limit crack depth $a_c$ is calculated on the basis of the fatigue crack growth characteristic diagram and the determining of the fatigue crack lifetime is performed on the basis of the calculated repetition count.

According to an eleventh aspect of the invention, in the method of determining a fatigue crack lifetime in a high-pressure hydrogen environment according to the seventh aspect, wherein the repetition count in which the initially-estimated crack depth $a_0$ reaches a predetermined depth with respect to the wall thickness is calculated on the basis of the fatigue crack growth characteristic diagram and the determining of the fatigue crack lifetime is performed on the basis of the calculated repetition count.

According to a twelfth aspect of the invention, in the method of determining a fatigue crack lifetime in a high-pressure hydrogen environment according to the tenth aspect, wherein the determining of the fatigue crack lifetime is performed on actual equipment depending on whether the repetition count in the actual equipment reaches the calculated repetition count.

According to a thirteenth aspect of the invention, in the method of determining a fatigue crack lifetime in a high-pressure hydrogen environment according to the seventh aspect, wherein the fatigue crack lifetime analysis is performed on the basis of a fatigue crack growth test which is performed in one or more repetition cycle times within a range of 15 s/cycle to 1000 s/cycle.

According to the invention, in the method of determining a fatigue crack lifetime of a material coming in contact with high-pressure hydrogen, the fatigue crack acceleration starting point $K_{max}^T$ of a test material is estimated using the crack-growth threshold stress intensity factor $K_{IH-R}$ obtained through the rising load test.

The inventor of the present invention found that the crack-growth threshold stress intensity factor $K_{IH-R}$ in high-pressure hydrogen obtained through the rising load test agrees to the fatigue crack acceleration starting point $K_{max}^T$ well. Therefore, it is possible to accurately estimate the fatigue crack acceleration starting point $K_{max}^T$ using the crack-growth threshold stress intensity factor $K_{IH-R}$. In this estimation, since $K_{IH-R}$ can be substantially considered as $K_{max}^T$ and the prediction error thereof is within ±10 MPa√m, the fracture of the pressure component can be predicted on the safety side by setting the safety-side estimated value of $K_{max}^T = K_{IH-R} - 10$ MPa√m.

At the high hydrogen pressure of about 90 MPa, particularly, 90 MPa or less, it is recognized that the agreement is excellent.

In the rising load test, a strain rate of dK/dt=0.08 MPa-m$^{1/2}$/s or less can be suitably set. The condition of the rising load test in the invention is not limited to specific ones, but may be set to a condition with the same pressure and atmosphere as in the high-pressure hydrogen environment in which $K_{max}^T$ is estimated and in which the test temperature tolerance between both environments is ±5° C. One or more conditions of a condition in which an ultrapure hydrogen (99.9999 vol % or more) environment is maintained, a condition in which an oxygen concentration is 1 ppm or less, and a condition in which the test temperature is 23° C.±5° C. are preferably satisfied. A compact test piece with a thickness of 1 inch having a crack formed in advance therein can be used as a test piece.

The crack-growth threshold stress intensity factor $K_{IH-R}$ may be obtained through a rising load test or may employ data known by literatures or the like.

The technique of obtaining the crack-growth threshold stress intensity factor $K_{IH-R}$ through the rising load test is disclosed, for example, in NPL 4. Specifically, when load-displacement diagrams in the atmosphere and the high-pressure hydrogen environment of a block test piece (1T-C(T) test piece) with a thickness of 1 inch having a crack formed therein are superimposed on each other, $K_{IH-R}$ is obtained from a point (deviation point) at which the diagram obtained in the high-pressure hydrogen environment deviates from the diagram obtained in the atmosphere and the load starts its decrease.

Data from the rising load test in the high-pressure hydrogen environment is disclosed, for example, in NPL 5. When it is difficult to perform the rising load test in the high-pressure hydrogen environment, the literature data may be used.

The result can be obtained from the rising load test for a still shorter time than from the delayed crack test which has been performed as the related-art method of determining a fatigue crack lifetime. Accordingly, it is possible to shorten the total time (for example, 1 hour) taken to determine the fatigue crack lifetime. A high-accuracy test result can be obtained from the rising load test regardless of the types of material. As a result, the accuracy of the evaluation of the fatigue crack lifetime is enhanced.

On the other hand, in the evaluation method employing the delayed crack test according to the related art, there is a problem in that the prediction accuracy of the fracture limit, that is, the fatigue crack acceleration starting point $K_{max}^T$, has a large deviation. The fatigue crack acceleration starting point $K_{max}^T$ can be obtained by performing a fatigue crack growth test. However, in this case, only when a test in from a short repetition cycle time to a long cycle time of about 150 s/cycle has to be carried out plural times, the fatigue crack acceleration starting point $K_{max}^T$ can be obtained with high accuracy, thereby requiring a long time.

By estimating the fatigue crack acceleration starting point $K_{max}^T$ from the crack-growth threshold stress intensity factor $K_{IH-R}$ which is obtained through the rising load test, the prediction accuracy of the fatigue crack acceleration starting point $K_{max}^T$ is improved, thereby shortening the time taken for the evaluation.

The fatigue crack lifetime analysis is performed using the fatigue crack acceleration starting point $K_{max}^T$ and the fatigue crack growth test result in high-pressure hydrogen.

The fatigue crack growth test in high-pressure hydrogen in the invention is not limited to a particular test, and can be performed, for example, in the following condition.

A fatigue testing machine equipped with an autoclave is used to measure the fatigue crack growth rate da/dN in the high-pressure hydrogen gas. An example of such a testing machine is reported already in NPL 6. Ultrapure hydrogen (99.9999 vol % or more) is used as hydrogen gas in any test, the gas purity in the test chamber is measured, and it is checked whether the oxygen concentration is 1 ppm or less. The fatigue crack growth test is carried out in a condition of constant load=ΔK gradual-increase or ΔK gradual-decrease. The crack length can be measured using an unloading elastic compliance method. The test temperature is designed using a thermostatic bath so as to maintain the environment at 23° C.(±5° C.) without varying during the long cycle-time test.

The fatigue crack growth test result may be obtained by actually performing the fatigue crack growth test or may be obtained with reference to data disclosed already in literatures and the like.

The fatigue crack growth characteristic diagram (da/dN-ΔK diagram) is obtained on the basis of the fatigue crack growth test result. The fatigue crack growth characteristic diagram may be obtained with reference to data disclosed already in literatures and the like.

The fatigue crack lifetime analysis can be performed in the section of $(1-R) \times K_0(a_0)$ to $(1-R) \times K_{max}^T(a_c)$ in the fatigue crack growth characteristic diagram (da/dN-ΔK diagram).

$(1-R) \times K_{max}^T$ corresponds to a bending point appearing in the da/dN-ΔK diagram as shown in FIG. 1. In the section (area I in FIG. 1), the fatigue crack growth does not depend on the repetition cycle time within a repetition cycle time range of 15 s/cycle to 1000 s/cycle.

$K_0$ represents the fatigue crack-growth threshold stress intensity factor and $K_{max}^T$ represents the fatigue crack acceleration starting point. $K_0(a_0)$ represents that the crack depth for expressing the crack-growth threshold stress intensity factor is the initially-estimated crack depth $a_0$ and $K_{max}^T(a_c)$ represents the fatigue crack acceleration starting point when the crack depth reaches the fracture-limit crack depth.

In the stress intensity factor range (area II in FIG. 1) larger than $(1-R) \times K_{max}^T(a_c)$, the fatigue crack growth starts acceleration and the growth rate depends on the repetition cycle time.

That is, according to the invention, as shown in FIG. 1, by dividing the fatigue crack growth characteristic diagram (da/dN-ΔK diagram) obtained in the high-pressure hydrogen into area I not depending on the repetition cycle time and area II depending on the repetition cycle time and performing the fatigue crack lifetime analysis in area I not depending on the repetition cycle time, it is possible to determine the fatigue crack lifetime.

In the step in which the crack opening is very small in area I of FIG. 1, since introduction of hydrogen molecules into the crack tip is regulated, the dependency on the repetition cycle time decreases, which is a feature thereof.

In the step equal to or more than $(1-R) \times K_{max}^T$ in area II of FIG. 1, since a hydrogen-assisted crack occurs in addition to the fatigue crack growth, appearance acceleration (bending) of da/dN is observed, which is a feature thereof In FIG. 1, evaluation can be performed when the stress ratio R varies. Accordingly, the invention can be applied to a case in which a pressure component is autofrettage-constructed and the like.

Since the fatigue crack growth characteristic of the section of $(1-R) \times K_0(a_0)$ to $(1-R) \times K_{max}^T(a_c)$ is hardly affected by the repetition cycle time in an arbitrary repetition cycle time in the range of 15 s/cycle to 1000 s/cycle, it is possible to accurately determine the fatigue crack lifetime of a material.

In the related art, when obtaining the fatigue crack acceleration starting point $K_{max}^T$, unless the fatigue crack growth test in from a short repetition cycle time to a long cycle time of about 150 s/cycle has to be carried out plural times by changing the condition of the repetition cycle time in the fatigue crack growth test, it is difficult to clearly distinguish the fatigue crack acceleration starting point $K\,max^{maxT}$.

However, in the invention, it is clear that the fatigue crack acceleration starting point $K_{max}^T$ has an excellent correlation with the crack-growth threshold stress intensity factor $K_{IH-R}$ obtained through the rising load test. As described above, the fatigue crack growth rate in area I which is a target area of the fatigue crack lifetime analysis in the invention does not depend on the repetition cycle time. Therefore, it is not necessary to perform the fatigue crack growth test plural times as in the related art, and it is possible to evaluate the characteristics in an arbitrary single repetition cycle time within a range of 15 s/cycle to 1000 s/cycle. That is, in order to obtain the fatigue crack growth characteristic through a test, the fatigue crack growth test in a short cycle time has only to be performed at least once.

DESCRIPTION OF EMBODIMENTS

Figure 2:
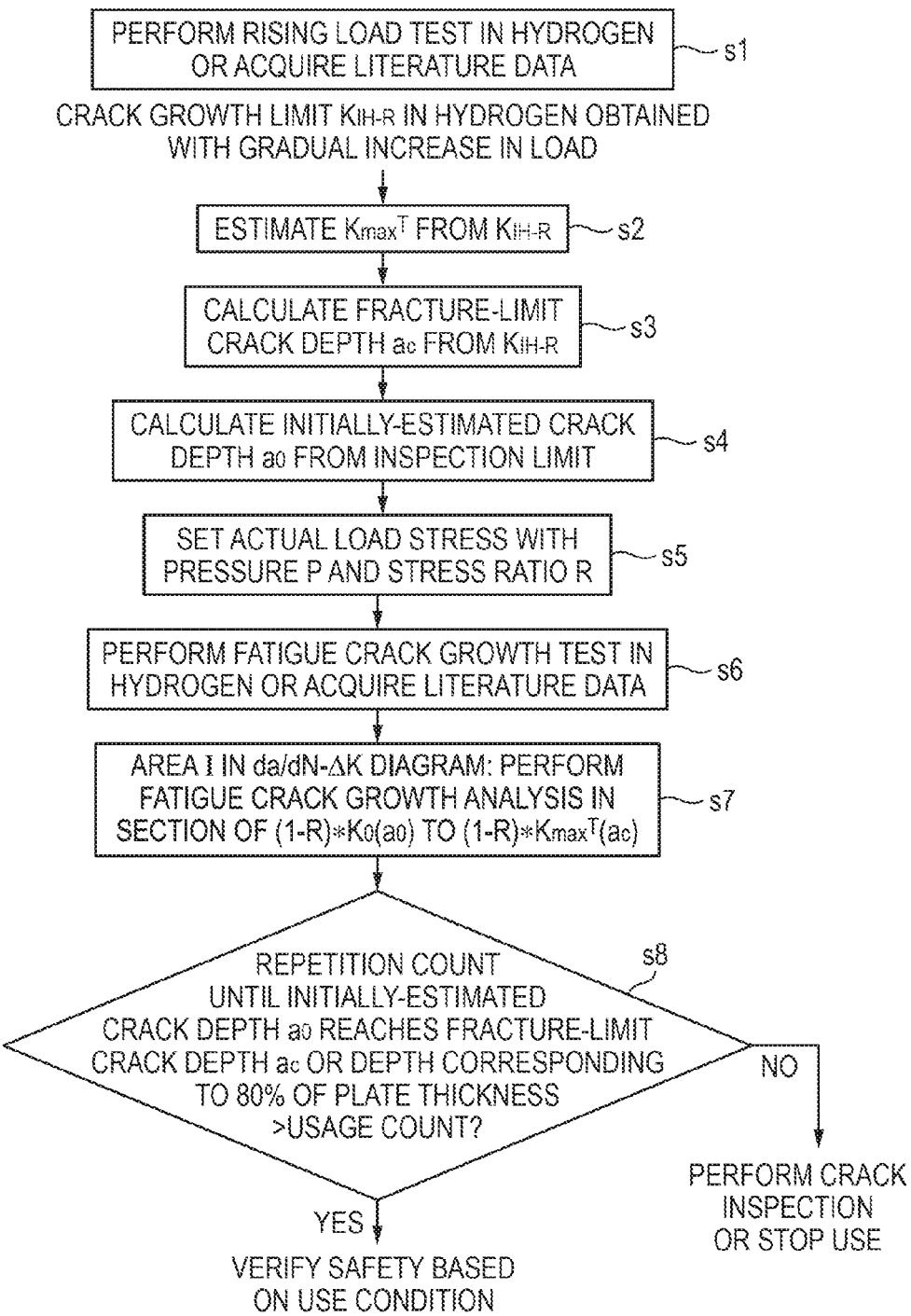
FIG. 2 is a flowchart illustrating a procedure of a method of determining a fatigue crack lifetime according to the invention.

The procedure of a method of determining a fatigue crack lifetime according to the invention will be described below with reference to FIG. 2.

First, a rising load test is performed on a test material in a hydrogen atmosphere (or literature data is acquired) and a crack-growth threshold stress intensity factor $K_{IH-R}$ of a hydrogen-assisted crack is obtained (step s1). In the rising load test, the test condition is set to a condition which has the same pressure and atmosphere as in a high-pressure hydrogen environment in which a fatigue crack acceleration starting point $K_{max}^T$ to be described later is estimated and in which the test temperature tolerance between both environments is ±5° C.

The fatigue crack acceleration starting point $K_{max}^T$ is estimated from the obtained crack-growth threshold stress intensity factor $K_{IH-R}$ (step s2). Since the crack-growth threshold stress intensity factor $K_{IH-R}$ and the fatigue crack acceleration starting point $K_{max}^T$ excellently agree to each other, the value of the crack-growth threshold stress intensity factor $K_{IH-R}$ is used as the value of the fatigue crack acceleration starting point $K_{max}^T$.

Then, a fracture-limit crack depth $a_c$ is calculated on the basis of the crack-growth threshold stress intensity factor $K_{IH-R}$ (step s3). The fracture-limit crack depth $a_c$ can be easily calculated using a calculation expression and a procedure of fracture mechanics known well in general. An example thereof will be described below (see NPL 7).

$a_c = K_{IH-R}^2 Q/(1.21 \pi \sigma^2)$ (where Q represents a defect shape factor and σ represents a stress)

Here, the defect shape factor Q is obtained as $Q = E_k^2 - 0.212(\sigma/\sigma ys)^2$ and $E_k^2 = 1 \pm 1.464(a/c)^{1.65}$ from the depth and length of the crack and the yield stress σys.

An initially-estimated crack depth ($a_0$) is estimated from an inspection limit in a predetermined inspection (step s4). Since the inspection limit varies depending on an inspection method or an inspection apparatus, the initially-estimated crack depth ($a_0$) can be calculated on the basis of an inspection method and an inspection apparatus performing a crack inspection using actual equipment.

The initially-estimated crack depth ($a_0$) may employ a value determined in a design guide of a pressure vessel disclosed in NPL 8. According thereto, the initially-estimated crack depth is 0.5 mm with a thickness of 16 mm or less, the initially-estimated crack depth is 1.1 mm with a thickness of equal to or more than 16 and less than 51 mm, and the initially-estimated crack depth is 0.6 mm with a thickness of 51 mm or more.

Then, the conditions of a pressure P and a stress ratio R (minimum load/maximum load) of the actual equipment are set (step s5).

Subsequently, the da/dN-$\Delta K$ diagram is obtained by performing a fatigue crack growth test in high-pressure hydrogen or from literature data (step s6).

A compact (C(T)) test piece with a thickness of 1 inch is used as a test piece, ultrapure hydrogen (99.9999 vol % or more) is used as the hydrogen gas in any test, the gas purity in a test chamber is measured, and it is checked whether an oxygen concentration is 1 ppm or less. The fatigue crack growth test may be performed using any of a condition of constant load=$\Delta K$ gradual-increase, $\Delta K$ gradual-decrease, and constant $\Delta K$.

In the obtained da/dN-$\Delta K$ diagram, the fatigue crack growth analysis is performed in the section of $(1-R) \times K_0(a_0)$ to $(1-R) \times K_{max}^T(a_c)$ (step s7).

In the fatigue crack growth analysis, the repetition count until the initially-estimated defect depth $a_0$ reaches a fracture-limit crack depth $a_c$ or a depth corresponding to 80% of the plate thickness before penetration is calculated. The repetition count can be easily calculated using a calculation expression and a procedure of fracture mechanics known well in general. An example thereof will be described below.

Figure 1:
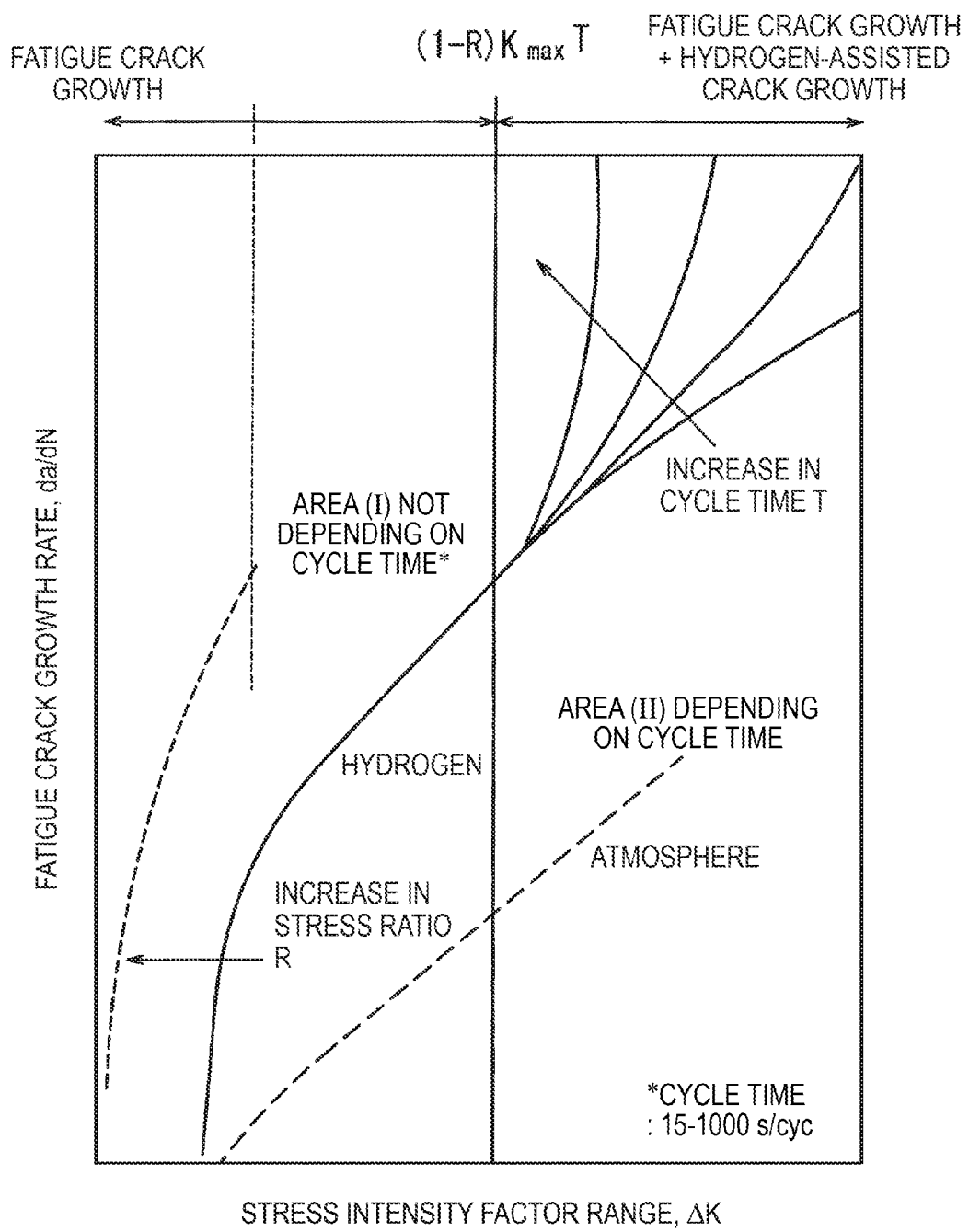
FIG. 1 is a fatigue crack growth characteristic diagram (da/dN-ΔK diagram) in high-pressure hydrogen according to the invention.

In both logarithmic diagrams of da/dN-$\Delta K$ (where da/dN represents a fatigue crack growth rate and $\Delta K$ represents a variation range of a stress intensity factor between repeated loads) shown in FIG. 1, a linear region is approximated by an expression $da/dN = C\Delta K^m$ (where C and m are constants) and the crack growth rate expression is integrated for each minute increment section of the crack to calculate the repetition count necessary for causing the crack to grow by the minute increment. By this repetition, the lifetime until the initially-estimated defect depth $a_0$ reaches the fracture-limit crack depth $a_c$.

The repetition count is compared with the usage count in actual equipment (step s8). When the calculated repetition count is larger than the usage count (YES in step s8), the safety based on the use condition is verified. On the other hand, when the usage count is larger than or equal to the repetition count (NO in step s8), the safety is not verified and thus a crack inspection is performed or the use thereof is stopped.

EXAMPLE 1

(Correlation between Fatigue Crack Acceleration Starting Point $K_{max}^T$ and Crack-growth Threshold Stress Intensity Factor $K_{IH-R}$)

As examples of low-alloy steel used for a steel pressure accumulator, SCM435 steel and SNCM 439 steel shown in Table 1 were subjected to heat treatment shown in Table 2 and were used as materials under test. Mechanical characteristics of the materials under test are shown in Table 2.

By performing a fatigue crack growth test in a high-pressure hydrogen environment of 90 MPa or less and evaluating the influence of the repetition cycle time, the fatigue crack acceleration starting point $K_{max}^T$ for each material under test was obtained.

A rising load test was performed on the same low-alloy steel and the crack-growth threshold stress intensity factor $K_{IH-R}$ was obtained. A delayed crack test was performed on the same low-alloy steel and the crack-growth threshold stress intensity factor $K_{IH-H}$ was obtained.

Figure 4:
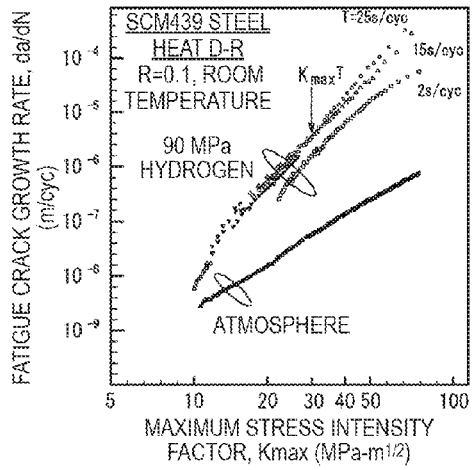
FIG. 4 is a diagram illustrating fatigue crack growth rates of a variety of low-alloy steel in high-pressure hydrogen gas.
Figure 4:
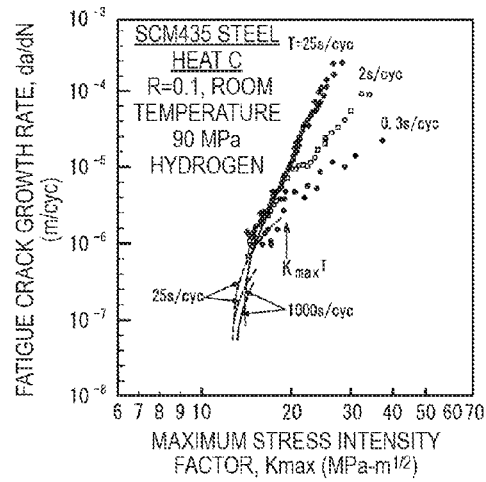
Figure 4:
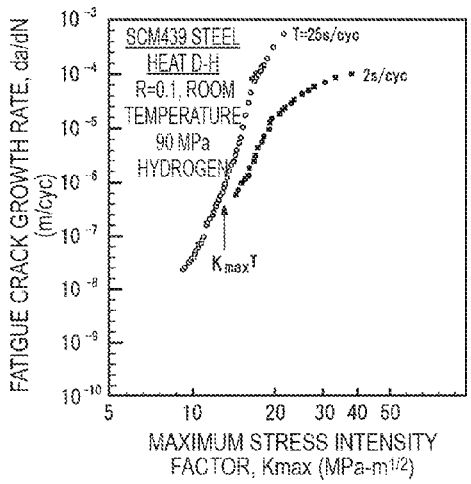
Figure 4:
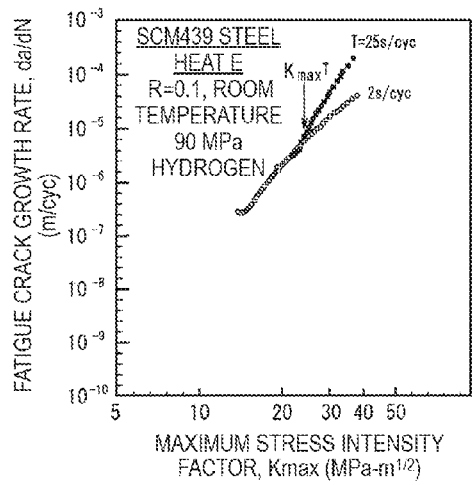

Details of the fatigue testing machine used in the fatigue crack growth test are disclosed in NPL 6. 200 kN hydraulic servo fatigue tester equipped with 45 MPa autoclave and 100 kN hydraulic servo fatigue tester equipped with 100 MPa autoclave were used to measure the fatigue crack growth rate da/dN in the high-pressure hydrogen gas. Details of the testers are disclosed in NPL 6 reported already. Ultrapure hydrogen (99.9999 vol % or more) was used as the hydrogen gas in any test, the gas purity in the test chamber was measured, and it was checked that oxygen concentration was 1 ppm or less. The fatigue crack growth test was performed with a stress ratio R of 0.1 and a condition of constant load=ΔK gradual-increase (some data in a diagram (b) in FIG. 4 is ΔK gradual-decrease) as long as not differently mentioned. An unloading elastic compliance method was used to measure the crack length. The test temperature was set to a room temperature of 23° C. (±5° C.).

Figure 3:
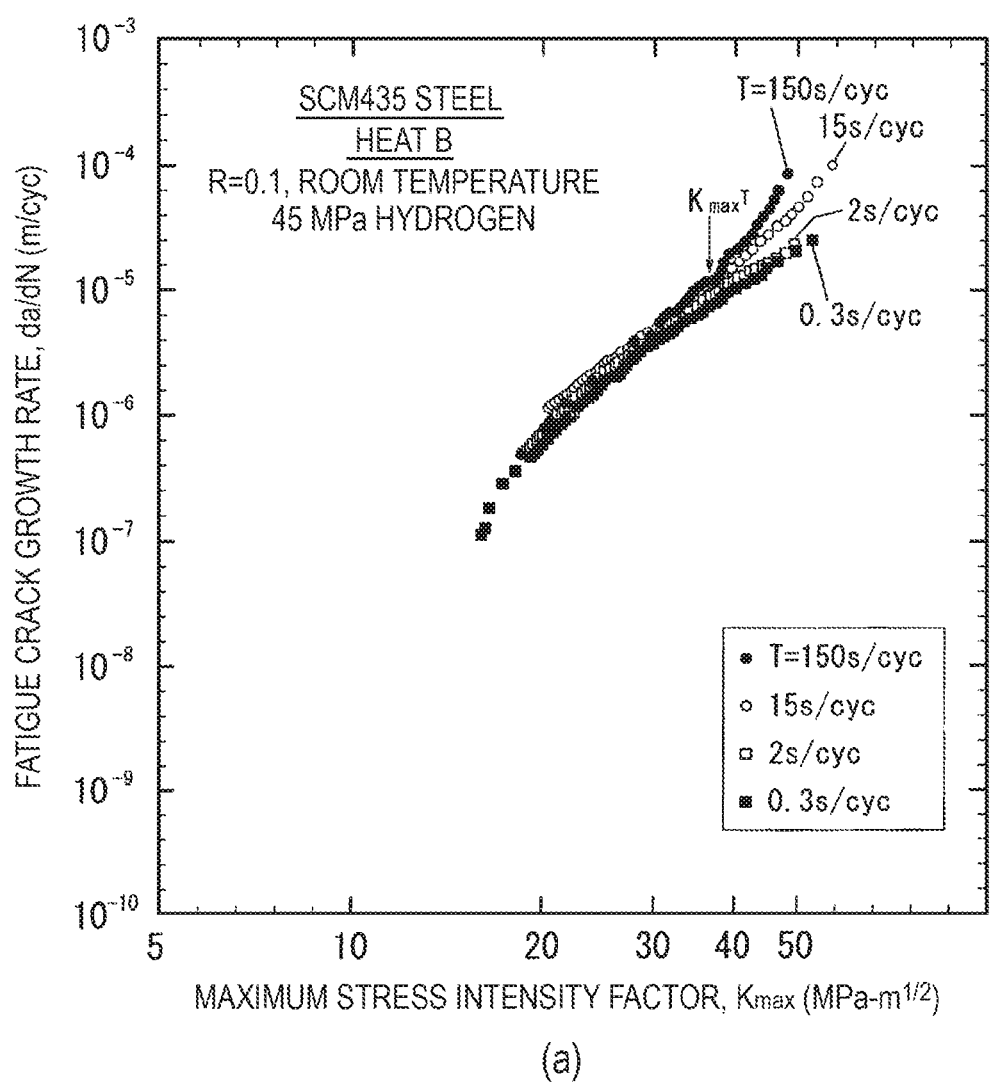
FIG. 3 is a diagram illustrating a fatigue crack growth rate of low-alloy steel in high-pressure hydrogen gas.

The results of the fatigue crack growth test are shown in a diagram (a) in FIG. 3, diagrams (b) to (e) in FIG. 4 and Table 3.

The fatigue crack growth rate in hydrogen exhibits a bending point in the da/dN-$K_{max}$ diagram, is accelerated as the repetition cycle time increases in area (II) of the K value larger than the bending point $K_{max}^T$, and is hardly affected in the repetition cycle time range of 15 s/cycle to 1000 s/cycle in area (I) of the K value smaller than $K_{max}^T$.

Figure 5:
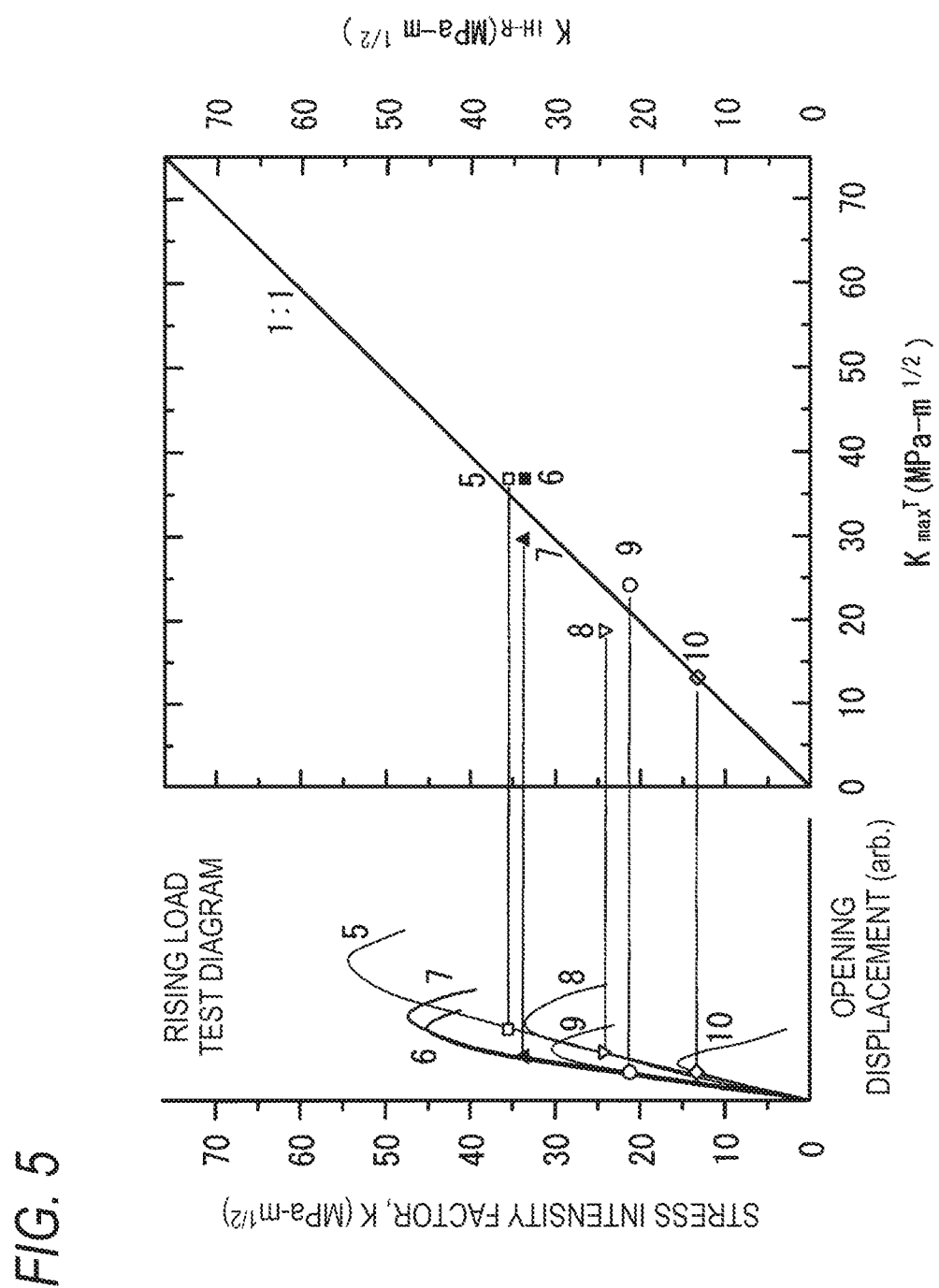
FIG. 5 is a diagram illustrating a correlation between a crack-growth threshold stress intensity factor $K_{IH-R}$ and a fatigue crack acceleration starting point $K_{max}^T$ obtained through a rising load test on a variety of low-alloy steel.
Figure 6:
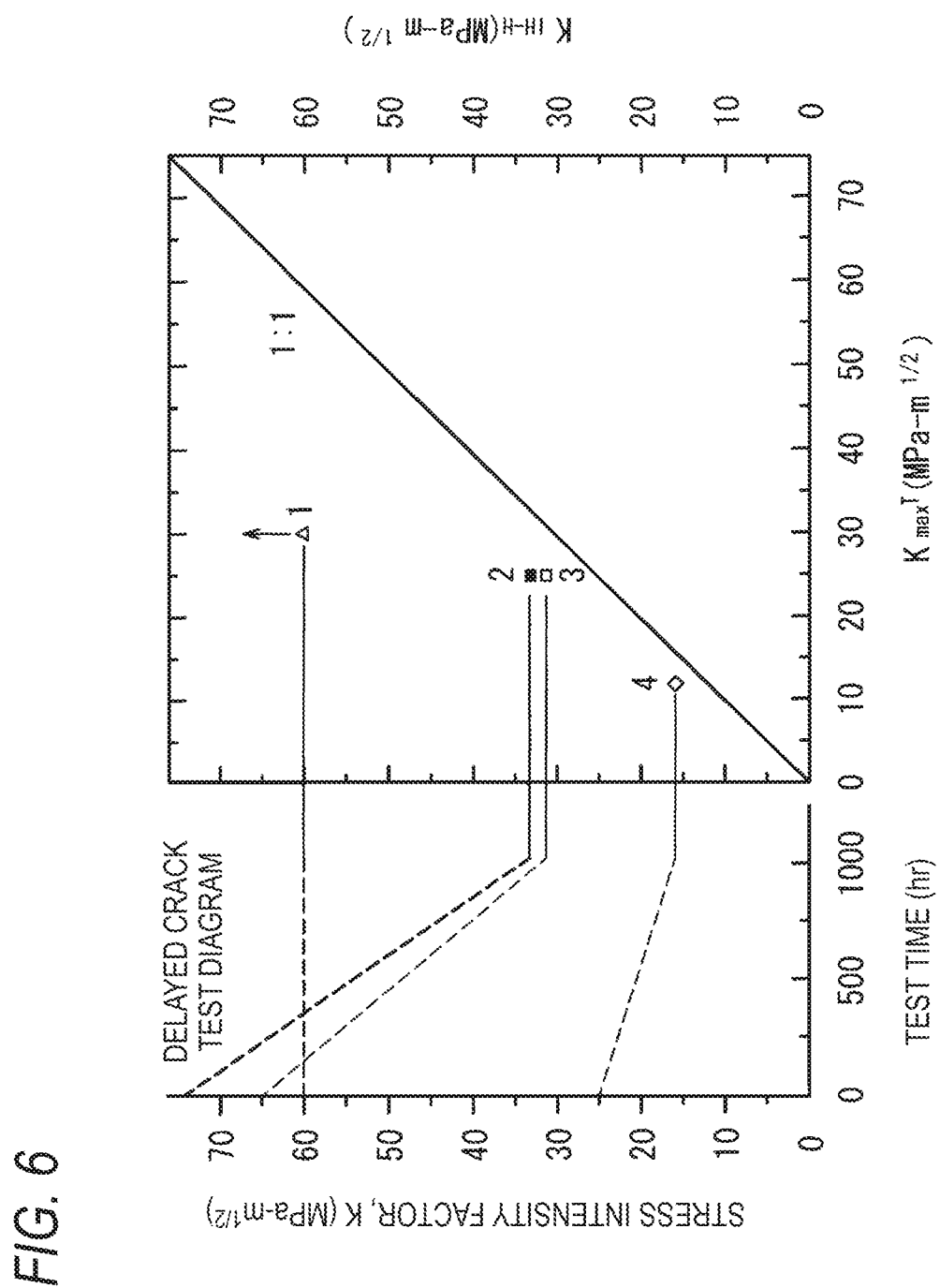
FIG. 6 is a diagram illustrating a correlation between a crack-growth threshold stress intensity factor $K_{IH-H}$ and a fatigue crack acceleration starting point $K_{max}^T$ obtained through a delayed crack test on a variety of low-alloy steel.

The fatigue crack acceleration starting point $K_{max}^T$ at which the fatigue crack growth starts its acceleration exhibits different values depending on differences between steel types, segregation states of materials, influences of material strength, and the like. However, it can be seen that the fatigue crack acceleration starting point $K_{max}^T$ exhibits excellent agreement in comparison with the crack-growth threshold stress intensity factor $K_{IH-R}$ obtained through the rising load test (FIG. 5). On the other hand, the agreement with the crack-growth threshold stress intensity factor $K_{IH-H}$ obtained through the related-art delayed crack test method is not observed (FIG. 6).

That is, as shown in Table 3, the crack-growth threshold stress intensity factor $K_{IH-H}$ obtained through the related-art delayed crack test method has a large deviation in prediction error of $K_{max}^T$. On the contrary, the deviation in prediction error is suppressed to the maximum 32% in the crack-growth threshold stress intensity factor $K_{IH-R}$ in the invention.

The crack-growth threshold stress intensity factor $K_{IH-R}$ obtained through the rising load test hardly varies even when the strain rate (dK/dt) is set to about 0.08 MPa-m$^{1/2}$/s and even when the strain rate is set to about 0.008 MPa-m$^{1/2}$/s smaller by one digit than the above-mentioned strain rate (FIG. 5). Therefore, the test can be finished for a short time depending on selection of the strain rate.

That is, the necessary time of the delayed crack test is 1000 hours, but the necessary test time can be reduced to 1 hour or less by employing the rising load test method, thereby enhancing the prediction accuracy and greatly reducing the test time.

TABLE 1

| Low-alloy steel | Heat treatment symbol (heat) | shape | Composition (wt %, balance Fe and inevitable impurities) | | | | | | | |
|---|---|---|---|---|---|---|---|---|---|---|
| | | | C | Si | Mn | P | S | Ni | Cr | Mo |
| SCM435 | A | Rolled sheet | 0.36 | 0.23 | 0.76 | 0.014 | 0.0100 | 0.03 | 1.06 | 0.19 |
| | B | Tube | 0.36 | 0.18 | 0.78 | 0.014 | 0.0025 | 0.01 | 1.12 | 0.26 |
| | C | Rolled rod | 0.37 | 0.30 | 0.76 | 0.025 | 0.0130 | 0.07 | 1.04 | 0.16 |
| SNCM439 | D | Forged sheet | 0.42 | 0.22 | 0.80 | 0.014 | 0.0023 | 1.82 | 0.86 | 0.25 |
| | E | Rolled rod | 0.40 | 0.23 | 0.78 | 0.022 | 0.0100 | 1.72 | 0.83 | 0.20 |
| | F | Forged rod | 0.40 | 0.26 | 0.80 | 0.005 | 0.0040 | 1.88 | 0.83 | 0.24 |

TABLE 2

| Low-alloy steel | Heat treatment symbol (heat) | Heat treatment condition | Tensile characteristic in air | | | Fatigue crack growth test |
|---|---|---|---|---|---|---|
| | | | $R_m$ (MPa) | $R_{p0.2}$ (MPa) | φ (%) | piece type/orientation |
| SCM435 | A | 850° C. O.Q., 510° C. T. and A.C. | 958 | 781 | 58 | C(T)/T-L(½ thickness) |
| | B | 900° C. O.Q., 550° C. T. and A.C. | 947 | 760 | 63 | C(T)/C-L(½ thickness) |
| | C | 880° C. W.S.Q., 560° C. T. and A.C. | 996 | 821 | 61 | C(T)/C-L(½ thickness)CY |
| SNCM439 | D-R | 850° C. Simulated cooling at 60° C./min., 640° C. T. and A.C. | 942 | 804 | 65 | C(T)/T-L(½ thickness) |
| | D-H | 850° C. O.Q., 580° C. T. and A.C. | 1144 | 1055 | 57 | C(T)/T-L(½ thickness) |
| | E | 870° C. O.Q., 620° C. T. and A.C. | 957 | 808 | 66 | C(T)/C-L(½ thickness) |
| | F | 860° C. O.Q., 590° C. T. and A.C. | 944 | 766 | 62 | C(T)/C-L(¼ thickness) |

O.Q.: Oil Quench, W.S.Q.: Water Spray Quench, T: Tempering, A.C.: Air Cooling
C(T): Compact Tension Test
CY: Cylinder Test Piece

TABLE 3

| Symbols shown in FIGS. 5 and 6 | Heat | Hydrogen pressure (MPa) | (1) Accelleration point of fatigue crack $K_{max}^T$ (MPa-m$^{1/2}$) | (2) Related-art method | | (3) Method according to the invention | | Prediction error (1)-((2) or (3)) |
|---|---|---|---|---|---|---|---|---|
| | | | | Test time (h) | $K_{IB-B}$ (MPa-m$^{1/2}$) | Test time*1 (h) | $K_{IH-R}$ (MPa-m$^{1/2}$) | |
| 1) | D-R | 90 | 30 | Strain is maintained for 1000 hours | 60 or more | — | — | −30 MPa or more |
| 2) | E | 90 | 25 | | 31 | — | — | +6 MPa |
| 3) | E | 90 | 25 | | 33 | — | — | +8 MPa |
| 4) | D-H | 90 | 13 | | 15.9*2 | — | — | +3 MPa |
| 5) | B | 45 | 37 | — | — | 0.12 | 35 | −2 MPa. |
| 6) | B | 45 | 37 | — | — | 1.22 | 33 | −4 MPa |
| 7) | D-R | 90 | 30 | — | — | 0.12 | 33 | +3 MPa |
| 8) | C | 90 | 19 | — | — | 0.12 | 24 | +5 MPa |
| 9) | E | 90 | 25 | — | — | 0.12 | 33 | +8 MPa |
| 10) | D-H | 90 | 13 | — | — | 0.12 | 13 | 0 MPa |

Figure 7:
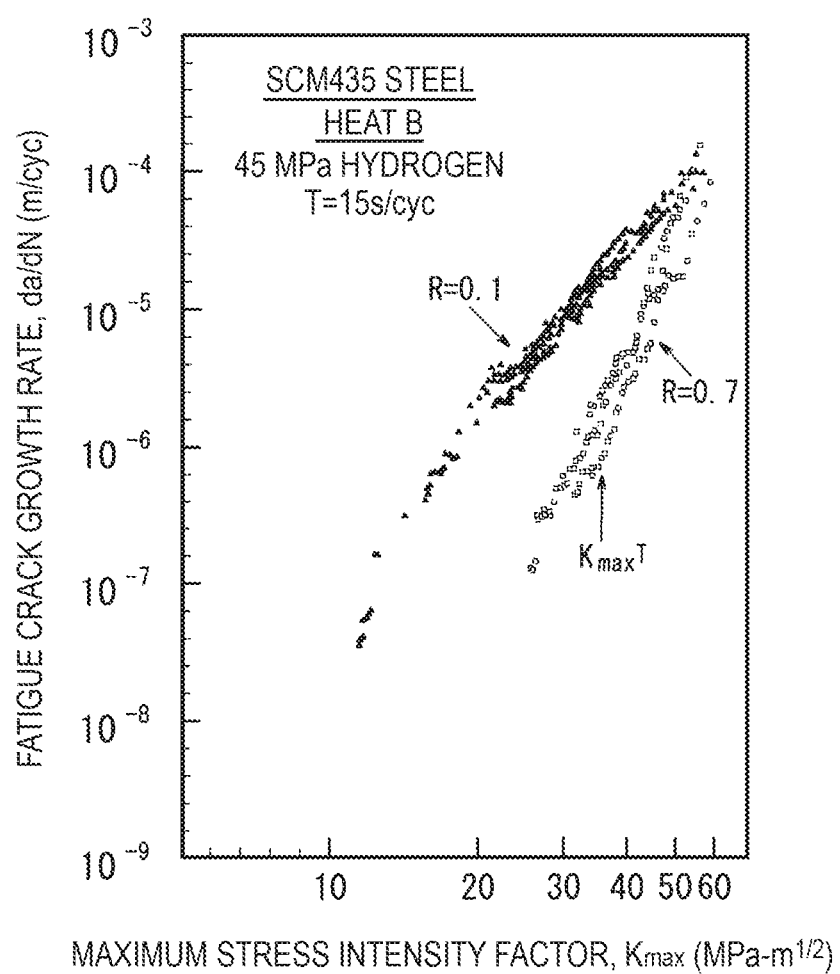
FIG. 7 is a diagram illustrating correspondence between the influence of a stress ratio on the fatigue crack growth rate and the fatigue crack acceleration starting point $K_{max}^T$.
Figure 8:
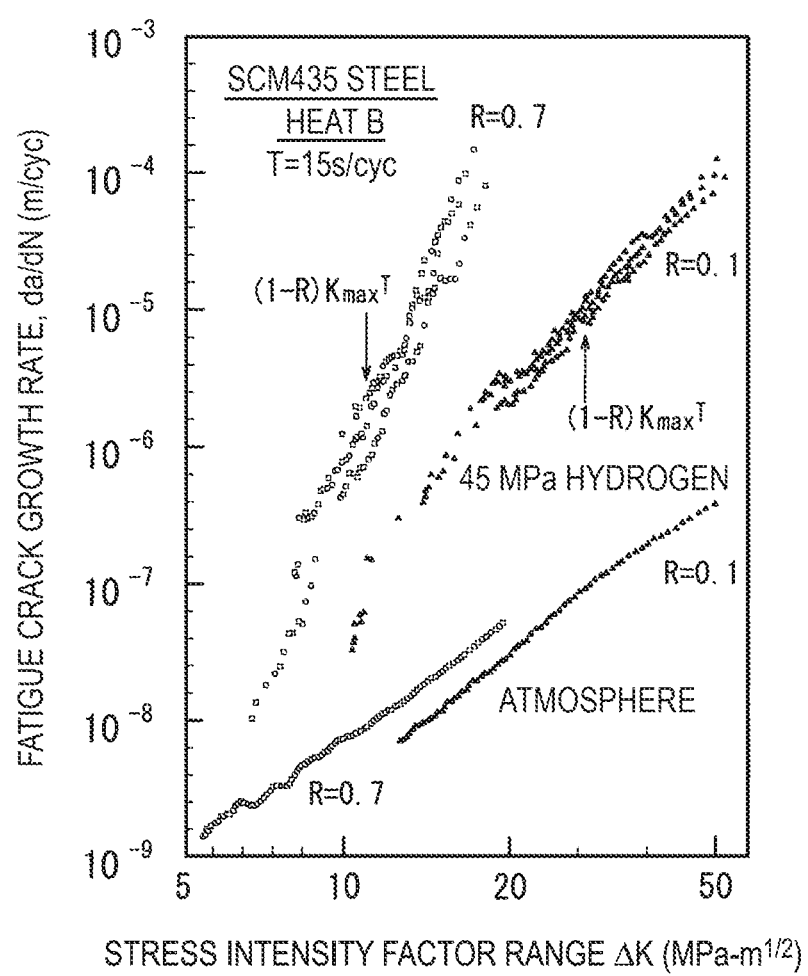
FIG. 8 is a fatigue crack growth characteristic diagram in which the horizontal axis of FIG. 7 is replaced with $\Delta K$.
Figure 9:
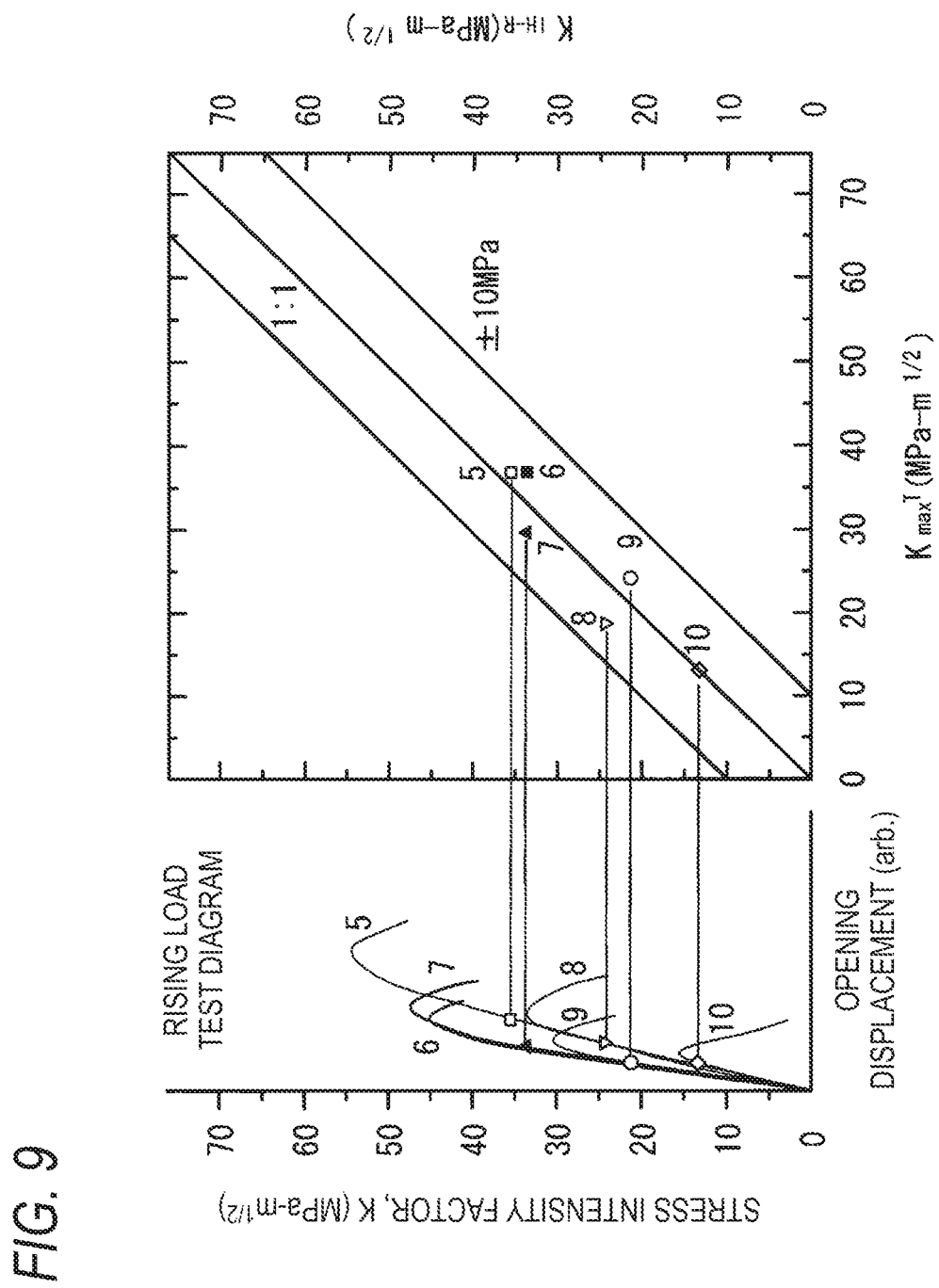
FIG. 9 is a diagram illustrating a procedure of evaluating $K_{IH-R}$ from the rising load test result and considering $K_{IH-R}$ as $K_{max}^T$ using FIG. 5.

*1 minimum test time calculated by strain rate (dK/dt) ÷ $K_{IH-R}$
dK/dt = 0.08 MPa-m$^{1/2}$ except for 6)
dK/dt = 0.008 MPa-m$^{1/2}$ in 6)
*2 test hydrogen pressure in related-art method (delayed crack test) is 85 MPa FIG. 7 shows the influence of a stress ratio on the fatigue crack growth rate in SNM435 steel (heat: B). In the cases having different stress ratios, the fatigue crack acceleration starting point $K_{max}^T$ can be estimated from the crack-growth threshold stress intensity factor $K_{IH-R}$ of a hydrogen-assisted crack obtained through the rising load test and the fatigue crack growth analysis can be performed.

(Example of Fatigue Crack Lifetime Determination according to the Invention)

An example where the fatigue crack lifetime determination is performed will be described below. The determination procedure is the same as the procedure shown in FIG. 2.

The low-alloy steel in this example is SNCM439 (heat: D-R) used in the above-mentioned example.

Figure 10:
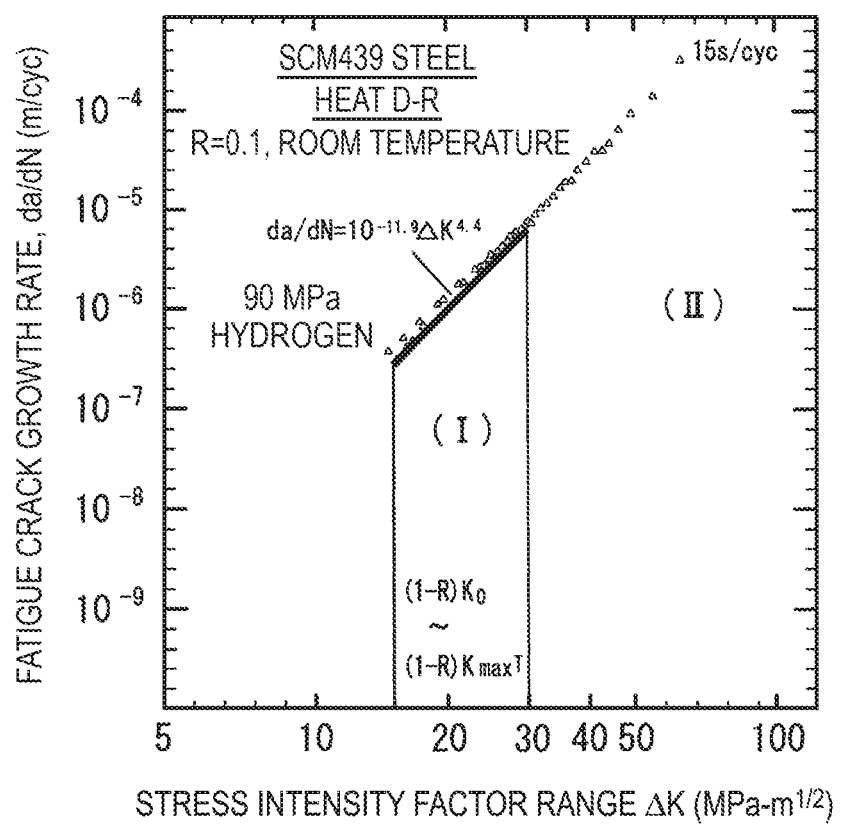
FIG. 10 is a diagram illustrating a procedure of performing a fatigue crack growth analysis in area I of the fatigue crack growth characteristic diagram (da/dN-$\Delta K$ diagram) according to an example of the invention.

In this example, as shown in Table 3 and FIG. 10, the crack-growth threshold stress intensity factor $K_{IH-R}$ is 33 MPa-m$^{1/2}$, the safety-side estimated value of $K_{max}^T = K_{IH-R} - 10$ MPa√m=(33−10) MPa√m=23 MPa√m is estimated, and the fracture-limit crack depth is calculated as $a_c$=4.5 mm.

The initially-estimated crack depth is set to $a_0$=1.6 mm from the inspection accuracy.

Regarding the setting of a load stress in actual equipment, it is assumed that a load with a pressure of P=80 MPa and a stress ratio of R=0.1 is repeatedly applied.

Subsequently, the fatigue crack growth test in hydrogen is performed to obtain fatigue crack growth characteristic data. At this time, by performing the test with a repetition cycle time of 15 s/cycle, the fatigue crack growth characteristic diagram (da/dN-ΔK diagram) shown in FIG. 10 is obtained.

Figure 11:
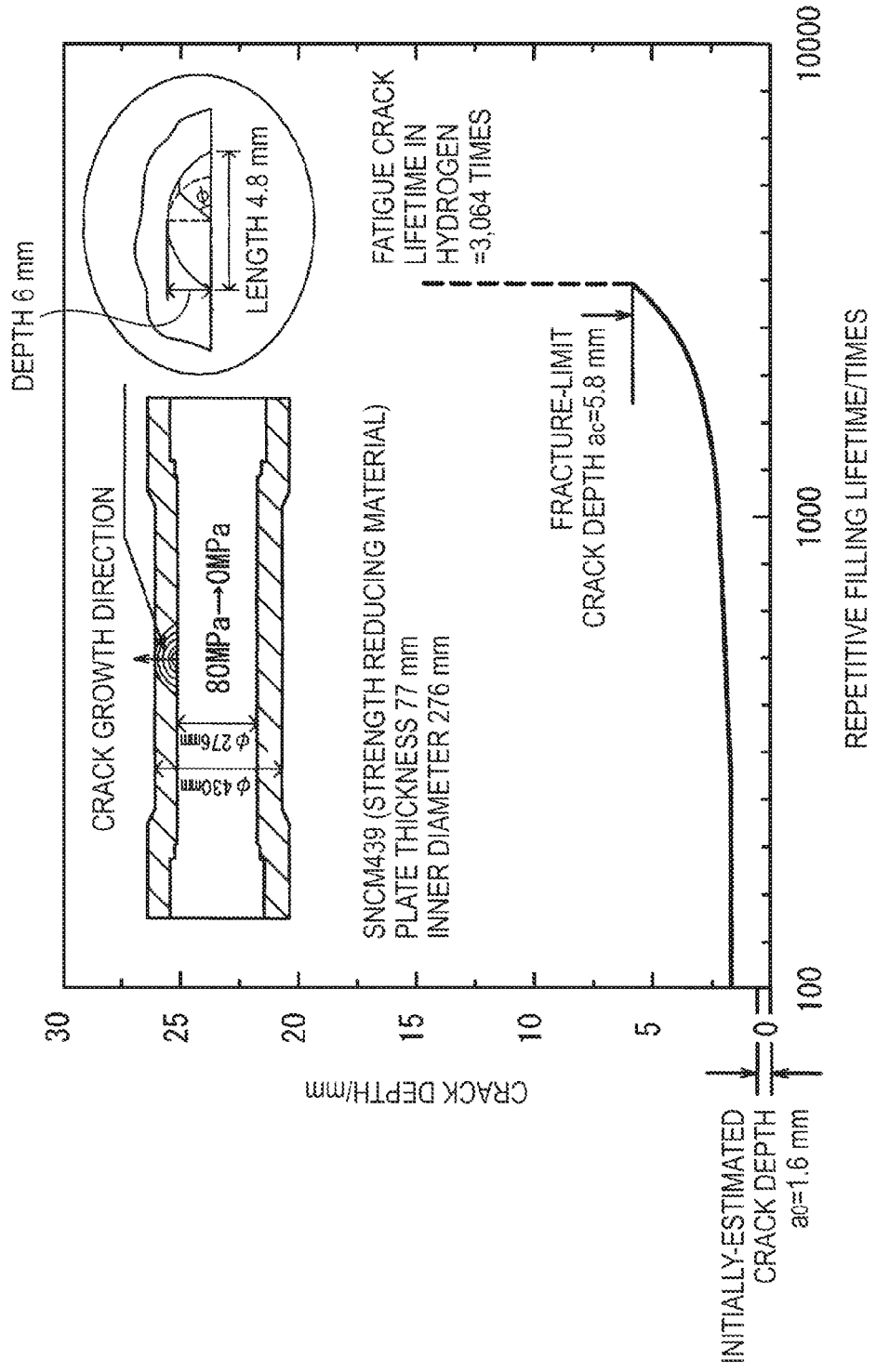
FIG. 11 is a diagram illustrating the fatigue crack growth analysis result and illustrating a relationship between the repetition count and the crack depth until the initially-estimated defect depth $a_0$ reaches a limit defect size $a_c$.
Figure 12:
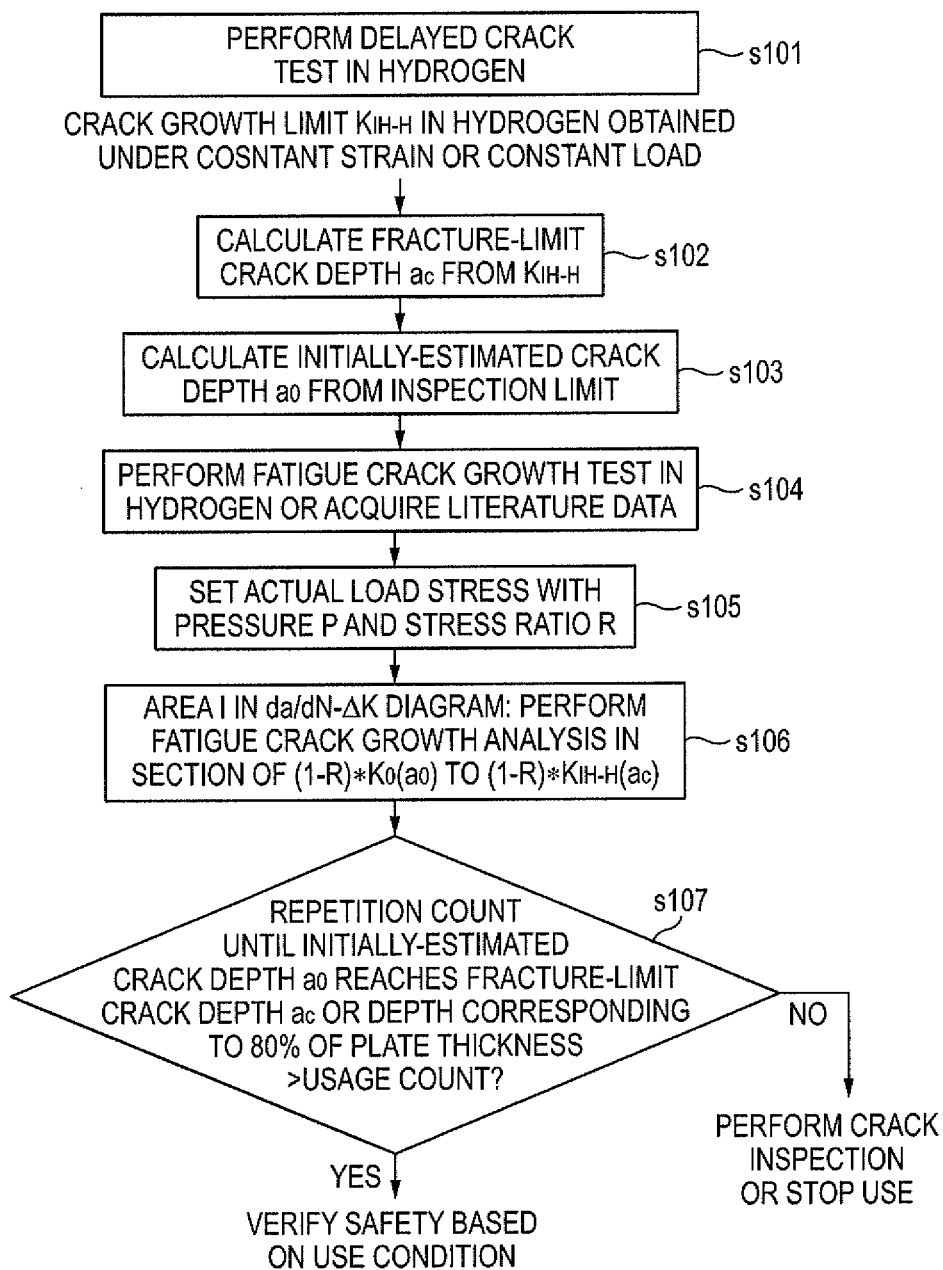
FIG. 12 is a flowchart illustrating a procedure of a method of determining a fatigue crack lifetime in a high-pressure hydrogen environment according to the related art.

Then, in area I, that is, the section of $(1-R) \times K_0(a_0)$ to $(1-R) \times K_{max}^T(a_c)$, of the obtained fatigue crack growth characteristic diagram (da/dN-ΔK diagram), the fatigue crack growth analysis is performed. The analysis result is shown in FIG. 11.

The actual value of $K_{max}^T$ is 30 MPa√m from the value of heat D-R in Table 3, and the actual fracture-limit crack depth $a_c$ is calculated as 5.8 mm. Therefore, the prediction error of the method according to the invention is 1.3 mm. On the other hand, in the related-art method, $K_{max}^T$ is 60 MPa√n or more from the value of heat D-R in Table 3, the actual fracture-limit crack depth $a_c$ is 22 mm or more, and thus an error of 15 mm or more occurs.

The invention is not limited to the above-mentioned embodiment, but may be appropriately modified and improved. In addition, materials, shapes, sizes, numerical values, forms, numbers, arrangement positions, and the like of elements in the above-mentioned embodiment are not particularly limited as long as the invention can be implemented.

While the invention has been described in detail with reference to a specific embodiment, it will be apparent to those skilled in the art that the invention can be modified and changed in various forms without departing from the spirit and scope of the invention.

This application is based on Japanese Patent Application (Application No. 2011-047417), filed on Mar. 4, 2011, contents of which are incorporated herein by reference.

Industrial Applicability

As described above, according to the invention, it is possible to determine a fatigue crack lifetime in high-pressure hydrogen with a small influence of materials or test conditions and with high accuracy for a short time.

The invention claimed is:

1. A method of determining a fatigue crack lifetime of a low-alloy steel material that comes in contact with high-pressure hydrogen in a high-pressure hydrogen environment, comprising: estimating a fatigue crack acceleration starting point $K_{max}^T$ of the low-alloy steel material using a crack-growth threshold stress intensity factor $K_{IH-R}$ obtained through a rising load test on the low-alloy steel material in a high-pressure hydrogen environment using hydrogen gas, wherein the high-pressure hydrogen environment of the rising load test is a high-pressure hydrogen environment which has the same pressure and atmosphere as in the high-pressure hydrogen environment in which $K^{maxT}$ is estimated and in which the test temperature tolerance between both environments is ±5° C.

2. The method of determining a fatigue crack lifetime in a high-pressure hydrogen environment according to claim 1, wherein the high-pressure hydrogen environment of the rising load test is an environment of ultrapure hydrogen of 99.9999 vol % or more.

3. The method of determining a fatigue crack lifetime in a high-pressure hydrogen environment according to claim 1, wherein the high-pressure hydrogen environment of the rising load test has an oxygen concentration of 1 ppm or less.

4. The method of determining a fatigue crack lifetime in a high-pressure hydrogen environment according to claim 1, wherein the test temperature of the rising load test is 23° C.±5° C.

5. The method of determining a fatigue crack lifetime in a high-pressure hydrogen environment according to claim 1, wherein the rising load test is performed at a strain rate of $dK/dt=0.08$ MPa-m$^{1/2}$/s or less for a short time (1 hour or less).

6. The method of determining a fatigue crack lifetime in a high-pressure hydrogen environment according to claim 1, wherein the estimating of the fatigue crack acceleration starting point is performed with a correlation that the fatigue crack acceleration starting point $K_{max}^{T}$ substantially agrees to the crack-growth threshold stress intensity factor $K_{IH\text{-}R}$.

7. The method of determining a fatigue crack lifetime in a high-pressure hydrogen environment according to claim 1 wherein a fatigue crack lifetime analysis is performed in a section of $(1-R) \times K_0(a_0)$ to $(1-R) \times K_{max}^{T}(a_c)$ in a fatigue crack growth characteristic diagram representing a relationship between a crack growth rate da/dN and a stress intensity factor width $\Delta K$ obtained through a fatigue crack growth test in a high-pressure hydrogen environment, wherein R represents a stress ratio, Mao) represents a fatigue crack-growth threshold stress intensity factor based on an initially-estimated crack depth ao, and $K_{max}^{T}(a_c)$ represents fatigue crack acceleration starting point based on a fracture-limit crack depth $a_c$.

8. The method of determining a faligue crack lifetime in a high-pressure hydrogen environment according to claim 7, wherein the initially-estimated crack depth is obtained from an inspection limit value based on a predetermined crack inspection.

9. The method of determining a faliguc crack lifetime in a high-pressure hydrogen environment according to claim 7, wherein the fracture-limit crack depth $a_c$ is calculated from the crack-growth threshold stress intensity factor $K_{IH\text{-}R}$.

10. The method of determining a fatigue crack lifetime in a high-pressure hydrogen environment according to claim 7, wherein a repetition count in which the initially-estimated crack depth $a_0$ reaches the fracture-limit crack depth $a_c$ is calculated on the basis of the fatigue crack growth characteristic diagram and the determining of the fatigue crack lifetime is performed on the basis of a calculated repetition count.

11. The method of determining a fatigue crack lifetime in a high-pressure hydrogen environment according to claim 10, wherein the determining of the fatigue crack lifetime is performed on actual equipment depending on whether a repetition count in the actual equipment reaches a calculated repetition count.

12. The method of determining a fatigue crack lifetime in a high-pressure hydrogen environment according to claim 7, wherein a repetition count in which the initially-estimated crack depth ao reaches a predetermined depth with respect to the wall thickness is calculated on the basis of the fatigue crack growth characteristic diagram and the determining of the fatigue crack lifetime is performed on the basis of a calculated repetition count.

13. method of determining a fatigue crack lifetime in a high-pressure hydrogen environment according to claim 7, wherein the fatigue crack lifetime analysis is performed on the basis of a fatigue crack growth test which is performed in one or more repetition cycle times wilhin a range of 15 s/cycle to 1000 s/cycle.

* * * * *